United States Patent
Visnovitz et al.

(10) Patent No.: US 12,429,489 B2
(45) Date of Patent: Sep. 30, 2025

(54) METHOD FOR DETERMINING THE LIPID CONTENT OF EXTRACELLULAR VESICLES

(71) Applicant: SEMMELWEIS EGYETEM, Budapest (HU)

(72) Inventors: Tamás Visnovitz, Dunaharaszti (HU); Xabier Osteikoetxea Velez, Budapest (HU); Edit Irén Buzás, Budapest (HU); Barbara Wernerné Sódar, Budapest (HU); Zoltán Varga, Inárcs (HU)

(73) Assignee: Semmelweis Egyetem, Budapest (HU)

( * ) Notice: Subject to any disclaimer, the term of this patent is extended or adjusted under 35 U.S.C. 154(b) by 1015 days.

(21) Appl. No.: 17/259,625

(22) PCT Filed: Jul. 12, 2019

(86) PCT No.: PCT/HU2019/050033
§ 371 (c)(1),
(2) Date: Jan. 12, 2021

(87) PCT Pub. No.: WO2020/012205
PCT Pub. Date: Jan. 16, 2020

(65) Prior Publication Data
US 2021/0293834 A1    Sep. 23, 2021

(30) Foreign Application Priority Data
Jul. 13, 2018    (HU) .................... P1800247

(51) Int. Cl.
G01N 33/92    (2006.01)
G01N 21/27    (2006.01)
G01N 21/78    (2006.01)

(52) U.S. Cl.
CPC ........... *G01N 33/92* (2013.01); *G01N 21/278* (2013.01); *G01N 21/78* (2013.01);
(Continued)

(58) Field of Classification Search
None
See application file for complete search history.

(56) References Cited

PUBLICATIONS

McMahon et al., The Spectrophotometric Sulfo-Phospho-Vanillin Assessment of Total Lipids in Human Meibomian Gland Secretions, 2013, Lipids. May 2013; 48(5): 513-525. (Year: 2013).*

(Continued)

*Primary Examiner* — Lyle Alexander
*Assistant Examiner* — Mickey Huang
(74) *Attorney, Agent, or Firm* — Jason D. Voight (57) ABSTRACT

The field of extracellular vesicles (EVs) currently attracts substantial attention in biomedicine due to the proposed role of EVs in various biological processes and their potential of serving as biomarkers for diseases. However, the availability of approaches for reliable and reproducible standardised quantification of EVs is limited. Therefore, current interest in EV research urges reliable tools of standardization and accurate enumeration of EVs, preferably on the basis of lipid quantification. By definition, EVs are surrounded by phospholipid bilayers, therefore, lipids (such as phospholipids and cholesterol) are essential components of all EVs. The method of the invention avoids the overestimation of EV concentration based on the protein measurement, as it focuses on the defining component of EVs, the lipid bilayer. Our method can be used virtually in any standard laboratories where a fume hood, a thermoblock, and a spectrophotometer are available. The application does not require expensive equipment, therefore it can be an easy, reliable and quick method for quantification of EVs and standardisation of EV experiments.

10 Claims, 3 Drawing Sheets

(52) U.S. Cl.
CPC ..... *G01N 2405/04* (2013.01); *G01N 2405/08* (2013.01); *G01N 2570/00* (2013.01)

(56) References Cited

PUBLICATIONS

Osteikoetxea et al., Improved Characterization of EV Preparations Based on Protein to Lipid Ratio and Lipid Properties, PLoS One. 2015; 10(3): e0121184. (Year: 2015).*

Vogel et al., A standardized method to determine the concentration of extracellular vesicles using tunable resistive pulse sensing, Journal of Extracellular Vesicles 2016, 5: 31242 (Year: 2016).*

Attwood et al., Preparation of DOPC and DPPC Supported Planar Lipid Bilayers for Atomic Force Microscopy and Atomic Force Spectroscopy, Int. J. Mol. Sci. 2013, 14, 3514-3539 (Year: 2013).*

* cited by examiner

METHOD FOR DETERMINING THE LIPID CONTENT OF EXTRACELLULAR VESICLES

This is the national stage of International Application PCT/HU2019/050033, filed Jul. 12, 2019.

BACKGROUND

The field of extracellular vesicles (EVs) currently attracts substantial attention in biomedicine due to the proposed role of EVs in various biological processes and their potential of serving as biomarkers for disease [1, 2, 3]. However, the availability of approaches for reliable and reproducible standardised quantification of EVs is limited [4, 5, 6]. Therefore, current interest in EV research urges reliable tools of standardization and accurate enumeration of EVs.

STATE OF THE ART

Quantifying EVs is not as straightforward as it seems. Commonly used methods for standardisation of EVs rely on measurement of total amount of proteins with colourimetric reactions (e.g. Micro BCA). One of the main problems of these techniques is that proteins may be co-isolated with EVs as protein aggregates, and EVs share biophysical parameters with them [7]. Therefore EV preparations are usually not sufficiently free of co-isolated proteins/protein aggregates to make such approaches reproducible or accurate (the apparent concentration of EVs in the preparations is therefore overestimated).

Tools available for particle enumeration and for the assessment of particle size and concentration include nanoparticle tracking analysis and tuneable resistive pulse sensing systems [6]. However, these methods are error-prone because they cannot distinguish vesicular and non-vesicular structures.

By definition, EVs are surrounded by phospholipid bilayers [5, 8], therefore, lipids (such as phospholipids and cholesterol) are essential components of all EVs. Ideally, lipid quantification would help to distinguish protein aggregates from EVs. Thus, it would help to avoid the overestimation of EV concentration based on the protein measurement, as it focuses on the defining component of EVs, the lipid bilayer. Quantification and standardisation of EV samples based on their lipid contents have been prevented until now by the lack of suitable methods; the measurement of lipid content has instead been expressed in relation to the amount of proteins in the sample as a measurement of sample purity.

Mihály et al [9] discloses a method for characterization of EVs wherein the protein/lipid (P/L) ratio can be determined using infrared (IR) spectroscopy but the technique is generally not available in most of the biomedical laboratories.

Osteikoetxea X et al [10] has disclosed a simple benchtop colourimetry-based lipid assay which is sufficient to determine lipid content of some EVs. It was also demonstrated that EV subtypes can be differentiated according to their protein/lipid ratio. The lipid assay is based on the well known sulpho-phospho-vanilin assessment (SPV). According to the article, the lipid assay shows higher intra and inter-assay variabilities than the protein assay when small amounts are measured. It is also confirmed by a recent review of Théry [6], it states that the broad use of this assay was limited by its relatively low sensitivity which implies that a significant proportion of an EV preparation was required for the lipid test, and it is difficult to keep enough for functional assays. According to the Théry review, combining quantification of total proteins and particle number is still the best way to quantify materials present in an EV preparation, even though the aforementioned problems of the protein measurements.

An alternative approach is mass spectroscopy (MS)-based lipid quantification, however, it still has strong dependence on equipment, requires higher sample amounts, long processing time and the technique may not be readily available to all laboratories [2].

Therefore, there is a need for improved, readily available and more sensitive benchtop methods of detecting and quantifying EVs, preferably on the basis of lipid quantification.

SUMMARY OF THE INVENTION

1. The present invention relates to a method for quantification of extracellular vesicles (EVs) in a sample comprising
   a) providing an EV preparation from the sample, the EV preparation being an aqueous suspension comprising EVs;
   b) contacting the EV preparation of step a) with sulphuric acid and subsequently with phospho-vanillin reagent and then allowing a colour reaction to develop, to obtain a coloured solution;
   c) measuring the absorbance of the resulting solution of step b) to obtain a preparation absorbance value, and measuring the absorbance of one or more reference solution prepared from a reference suspension to obtain a reference absorbance value;
   d) comparing the preparation absorbance value and the one or more reference absorbance value measured in step c) and determining the amount of lipids in the EV preparation from the result of said comparison;
   e) determining the amount of EVs in the EV preparation of step a) from the amount of lipid calculated in step d);
   characterized in that EV preparation in step a) is substantially free of organic solvents; the reference suspension in step c) is a suspension comprising a reference material suspended in aqueous solvent, the reference material is a phospholipid capable of forming liposomes, preferably 1,2-dioleoyl-sn-glycero-3-phosphocholine (DOPC), sphingomyelin, phosphatidyl serine or phosphatidyl etanolamine; and the reference suspension is substantially free of organic solvents.

2. The present invention also relates to a method for quantification of lipids in a sample comprising extracellular vesicles (EVs), the method comprising the steps of
   a) providing an EV preparation from the sample, the EV preparation being an aqueous suspension comprising EVs;
   b) contacting the EV preparation of step a) with sulphuric acid and subsequently with phospho-vanillin reagent and then allowing a colour reaction to develop, to obtain a coloured solution;
   c) measuring the absorbance of the resulting solution of step b) to obtain a preparation absorbance value, and measuring the absorbance of one or more reference solution prepared from a reference suspension to obtain a reference absorbance value;
   d) comparing the preparation absorbance value and the one or more reference absorbance value measured in step c) and determining the amount of lipids in the EV preparation from the result of said comparison;
   characterized in that EV preparation in step a) is substantially free of organic solvents; the reference suspension in step c) is a suspension comprising a reference material suspended in aqueous solvent, the reference material is a phospholipid capable of forming liposomes, preferably 1,2-dioleoyl-sn-glycero-3-phosphocholine (DOPC), sphingomyelin, phosphatidyl serine or phosphatidyl etanolamine; and the reference suspension is substantially free of organic solvents.

3. In a preferred embodiment of any of the methods above, the reference suspension in step c) is a diluted stock suspension, wherein the stock suspension comprising the reference material is suspended in aqueous solvent, and the stock suspension is substantially free of organic solvents.

4. In a preferred embodiment of any of the methods above, the EV preparation of step a) contains EVs having a size range wherein the difference between the lower limit and the upper limit of the range is lower than 600 nm, preferably lower than 500 nm, 400 nm, 300 nm, 200 nm or 100 nm.

5. In a preferred embodiment of the method according to any of the above points 1 to 3, the EV preparation of step a) contains EVs in the size range of less than 200 nm or from 100 nm to about 800 nm or from 800 nm to about 5000 nm.

6. Method according to any of the above points 1 to 5, wherein the solvent of the aqueous suspension is an aqueous buffer, for example PBS, NaCl-HEPES, MES, TRIS, physiological NaCl solution or Dulbecco's PBS (DPBS), preferably PBS or NaCl-HEPES.

7. Method according to any of the above points 1 to 6, wherein the reference suspension and the stock suspension are suspended in an aqueous buffer, for example PBS, NaCl-HEPES, MES, TRIS, physiological NaCl solution or DPBS, preferably PBS or NaCl-HEPES.

8. Method according to any of the above points 1 to 7, wherein the sample is a body fluid sample or cell culture sample.

9. Method according to any of the above points 1 to 8, wherein step b) comprises
   b1) contacting the solution of step a) with sulphuric acid and mixing with vortex
   b2) incubating the mixture of b1) at 90° C. for 20 min, then cooling to room temperature
   b3) adding phospho-vanillin reagent and mixing with vortex
   b4) incubating the mixture of b3) for 1 h at 37° C. to enable the colour reaction to develop.

10. Method according to any of the above points 1 to 9, wherein the absorbance is measured at 540 nm.

11. Method according to any of the above points 1 to 10, wherein the method is performed in a container being suitable for the SPV reaction.

12. The present invention also relates to a method for quantification of biological membranes in a sample comprising
   a) providing a preparation from the sample, the preparation comprising biological membranes in an aqueous suspension;
   b) contacting the preparation of step a) with sulphuric acid and subsequently with phospho-vanillin reagent and then allowing a colour reaction to develop to obtain a coloured solution;
   c) measuring the absorbance of the resulting solution of step b) to obtain a preparation absorbance value, and measuring the absorbance of one or more reference solution prepared from a reference suspension to obtain a reference absorbance value;
   d) comparing the preparation absorbance value and the one or more reference absorbance value measured in step c) and determining the amount of lipids in the preparation from the result of said comparison;
   e) determining the amount of membranes in the preparation of step a) from the amount of lipid calculated in step d);
   characterized in that the preparation in step a) is substantially free of organic solvents; the reference suspension in step c) is a suspension comprising a reference material suspended in aqueous solvent, the reference material is a phospholipid capable of forming liposomes, preferably 1,2-dioleoyl-sn-glycero-3-phosphocholine (DOPC), sphingomyelin, phosphatidyl serine or phosphatidyl etanolamine; and the reference suspension is substantially free of organic solvents.

13. The present invention also relates to a method for quantification of lipids in a sample containing biological membranes, the method comprising the steps of
   a) providing a preparation from the sample, the preparation comprising biological membranes in an aqueous suspension;
   b) contacting the preparation of step a) with sulphuric acid and subsequently with phospho-vanillin reagent and then allowing a colour reaction to develop to obtain a coloured solution;
   c) measuring the absorbance of the resulting solution of step b) to obtain a preparation absorbance value, and measuring the absorbance of one or more reference solution prepared from a reference suspension to obtain a reference absorbance value;
   d) comparing the preparation absorbance value and the one or more reference absorbance value measured in step c) and determining the amount of lipids in the preparation from the result of said comparison;
   characterized in that the preparation in step a) is substantially free of organic solvents; the reference suspension in step c) is a suspension comprising a reference material suspended in aqueous solvent, the reference material is a phospholipid capable of forming liposomes, preferably 1,2-dioleoyl-sn-glycero-3-phosphocholine (DOPC), sphingomyelin, phosphatidyl serine or phosphatidyl etanolamine; and the reference suspension is substantially free of organic solvents.

14. In a preferred embodiment of the methods in points 12 or 13, the reference suspension in step c) is a diluted stock suspension, wherein the stock suspension comprising the reference material is suspended in aqueous solvent, and the stock suspension is substantially free of organic solvents.

15. The present invention also relates to the use of a reference suspension being a suspension comprising a reference material suspended in aqueous solvent, the reference material is a phospholipid capable of forming liposomes, preferably 1,2-dioleoyl-sn-glycero-3-phosphocholine (DOPC), sphingomyelin, phosphatidyl serine or phosphatidyl etanolamine; and the reference suspension is substantially free of organic solvents; for quantifying extracellular vesicles (EVs) in a sample or preparation.

16. The present invention also relates to the use of a reference suspension being a suspension comprising a reference material suspended in aqueous solvent, the reference material is a phospholipid capable of forming liposomes, preferably 1,2-dioleoyl-sn-glycero-3-phosphocholine (DOPC), sphingomyelin, phosphatidyl serine or phosphatidyl etanolamine; and the reference suspension is substantially free of organic solvents; for quantifying lipids in a sample or preparation comprising extracellular vesicles (EVs).

17. The present invention also relates to the use of a reference suspension being a suspension comprising a reference material suspended in aqueous solvent, the reference material is a phospholipid capable of forming liposomes, preferably 1,2-dioleoyl-sn-glycero-3-phosphocholine (DOPC), sphingomyelin, phosphatidyl serine or phosphatidyl etanolamine; and the reference suspension is substantially free of organic solvents; for quantifying lipids in a sample or preparation comprising biological membranes.

18. The present invention also relates to a kit comprising a reference suspension being a suspension comprising a reference material suspended in aqueous solvent, the reference material is a phospholipid capable of forming liposomes, preferably 1,2-dioleoyl-sn-glycero-3-phosphocholine (DOPC), sphingomyelin, phosphatidyl serine or phosphatidyl etanolamine; and the reference suspension is substantially free of organic solvents. The kit also includes at least one manual (instruction manual) about the inspection. The kit can be used for carrying out the method according to any of the points above. The kit may contain a container or containers being suitable for the SPV reaction.

BRIEF DESCRIPTION OF FIGURES

FIG. 1: Standard curve of the improved lipid assay

DETAILED DESCRIPTION OF THE INVENTION

Extracellular vesicles (EVs) are phospholipid bilayer enclosed particles which are produced by both eukaryotic and prokaryotic cells. These membranous vesicles are secreted by various types of cells. Extracellular vesicles include (i) exosomes or small EVs (sEVs), membranous vesicles usually smaller than 200 nm in diameter that are secreted by a wide range of cell types, (ii) microvesicles or mid-sized EVs (mEVs), 100 to about 800 nm in diameter that are released directly from plasma membranes, and (iii) apoptotic bodies or large EVs (lEVs), 800 to 5000 nm in diameter. As it comes from the above definitions, EVs in general are smaller than or equal to 5000 nm.

The sample origin may be a body fluid sample or cell culture sample. The body fluid may be, for example, urine, mucus, saliva, tears, blood plasma, blood serum, sputum, spinal fluid, hydrothorax, nipple aspirate, lymph, tracheolar fluid, intestinal fluid, genitourinary tract fluid, breast milk, lymph system fluid, semen, cerebrospinal fluid, tracheal system fluid, ascites, cystic tumor fluid, amniotic fluid, or any combination thereof. The cell culture may be any conditioned medium and preferably the medium does not contain fetal calf serum (FCS or FBS) or other animal products, to avoid e.g. co-isolation of FCS-derived EVs.

The term "providing an EV preparation" includes harvesting an EV-containing fluid from tissue culture sample or from a body fluid sample and separating the EVs from other non-EV components (for example cells) of the biofluid or conditioned medium. Therefore this term includes the feature that the EV preparation is purified, i.e. the amount of non-EV components is reduced or these components are preferably eliminated. The term "harvesting" is intended to mean that the EV-containing fluid is withdrawn from the cell culture sample or from a body fluid sample and optionally processed for further use. The cell culture sample or body fluid sample (or pellets prepared therefrom) may be washed one or more times, for example in PBS (phosphate buffered saline) or any other aqueous buffer. The EV-containing fluid may be harvested by obtaining the supernatant containing the EVs. The EV-containing fluid may be centrifuged to remove the cells or other non-EV components and to obtain the supernatant. The sample may then be subjected to gravity driven filtration. In summary, the term "providing an EV preparation" includes removing cells, preferably removing lipids of non-EV origin and obtaining cell free (EV) suspension.

The processing of the sample to obtain EV preparation may include the separation of different types of EVs (sEVs, mEVs and lEVs) from each other. Overall, the EV preparation covers such a suspension which is enriched in EVs, preferably where the size range of EVs are narrow (see below); however it may contain soluble proteins and protein aggregates and may contain EVs of other type in minor amount, but non-EV components or cells are substantially eliminated.

For the separation of EVs from other non-EV components and for separation of different types of EVs ultracentrifugation or differential ultracentrifugation is the most commonly used technique. However, various other techniques, such as density gradient, precipitation, filtration, chromatography, for example size exclusion chromatography and immune-affinity based isolation are available. In some embodiments of the invention, the EV sample may be separated into size fractions other than the above mentioned fractions. Using the described techniques, EVs of any size range can be separated from the sample. In a preferred embodiment, the EV sample are processed/separated to contain EVs being in a narrow size range, i.e. in a range wherein the difference between the lower limit and the upper limit of the range is lower than 600 nm, preferably lower than 500 nm, 400 nm, 300 nm, 200 nm or 100 nm, for example in the size range of 700 to 900 nm.

The contacting in step b) may be performed in vitro. The combined step b) and c) is known as the sulfo-phospho-vanillin (SPV) assay. The basics of this assay can be found in the article of Frings and Dunn (1970, AJCP A Colorimetric Method for Determination of Total Serum Lipids Based on SPV reaction). In the present invention, concentrated $H_2SO_4$ is added to a tube containing the sample, mixing (for example vortexing) and heating the tube for 10-30 minutes at 80-100° C. The acid treatment results in the formation of solution (suspension→solution). Then the tube is cooled down to room temperature (for example by placing it for at least 5 min at 4° C.). The phospho-vanillin reagent is added to the cooled solution and the resulting solution is mixed (vortex). Finally, the sample may be transferred to a 96 well plate and it is incubated for 15-90 minutes at 15-50° C. allowing the colour to develop. The absorbance is measured with an absorbance reader, preferably a plate reader at a suitable wavelength, preferably at 540 nm.

In the SPV assay, interfering compounds may be formed from plastic components and possible coating or wall residues of the test container due to the presence of acids. Careful selection of the container suitable for the SPV assay is important. A container is suitable for the SPV assay if an analysis is performed according to the invention in the container with the reagents but without the EV preparation and the calculated lipid amount is below the limit of quantification and preferably below the limit of detection. The EV preparation is replaced in this test with the aqueous buffer of said preparation in the same volume. An example for containers which are not suitable for SPV assay include LoBind T330-7LST Simport, Canada. It contains surface coats that interact with components of the assay and cause artefacts.

The term "stock suspension" refers to a suspension made from a precisely known quantity of pure compound (reference material) suspended in a known volume of solvent, in the present case aqueous buffer, for example PBS, usually at a 0.1-10 mg/ml concentration level. The stock suspension is stable, meaning that it does not separate into aqueous and organic fractions for at least 24 hours, or preferably at least 7 days with no mixing after an initial suspension step. The stock suspension used in the present invention contains a reference material suspended in aqueous solution or buffer. The reference material can be any suitable phospholipid forming stable liposomes, for example 1,2-dioleoyl-sn-glycero-3-phosphocholine (DOPC), sphingomyelin and further phospholipids such as such phosphatidyl serine, phosphatidyl etanolamine. Preferably, the phospholipids forming stable liposomes contain a double bond in one or more of the alkyl chains. The aqueous solution or buffer suspending the reference material is for example PBS, NaCl-HEPES, DPBS, MES, TRIS and physiological NaCl solution, preferably PBS or NaCl-HEPES. The stock suspension is substantially free of organic solvents.

The term "suspension" refers to a dispersion of a substance or substances in a solvent where the material has limited solubility in that solvent. The boundaries between the dispersed substance and the solvent are well defined. The suspension of the invention can be considered also as an emulsion, depending on whether the vesicle or the reference material is considered solid or liquid. Disperse systems containing vesicles are generally referred to in the prior art as "suspensions", however the disperse system of reference material according to the invention is referred to as both emulsions and suspensions. Therefore the terms "suspension" and "emulsions" are used interchangeably throughout the present specification in connection with the disperse system containing vesicles and/or reference materials.

The term "reference" suspension refers to a diluted suspension of the stock suspension where the concentration of the reference material is known. The reference suspension can be prepared by adding a precise volume of a stock suspension to a precise volume of (aqueous) solvent. The reference suspension is subjected to the same steps of the SPV reaction as the EV preparation (or other preparation), i.e. contacting it with sulphuric acid and subsequently with phospho-vanillin reagent and then allowing the colour reaction to develop; and measuring the absorbance of the resulting solution. In short, the reference suspension is also subjected to step b) to obtain a reference solution. The reference suspension is substantially free of organic solvents. The reference suspension may be prepared right before the assay or applied as a ready-to-use suspension available commercially.

The term "substantially free" means that the solution preferably contains organic solvent in a negligible amount that causes no yellow coloration in the SPV assay when no phospho-vanillin reagent was added. More precisely, the "no yellow coloration" means (i.e. when the suspension is substantially free of organic solvents) that if a reaction is performed in the container between the reference solution or the EV preparation with sulphuric acid but without phospho-vanillin reagent, the absorbance of the resulting solution is about 20% of the lowest concentration of the reference suspension measured according to the invention (i.e. to which phospho-vanillin reagent is also added).

As used herein, the term "quantification" refers to determining the amount of EVs present in the EV preparation. The (relative) quantification requires reference suspensions with certain concentrations and based on the measurement of the absorbances of the solution of step b) and that of the reference suspension subjected to the same steps and comparing said absorbances. When more than one reference suspension was measured, the data—the concentrations of the reference material in the reference suspension and the instrument response for each reference suspension—can be fit to a straight line (calibration curve) using linear regression analysis. The concentration of analyte (lipids in EV preparation) can be determined with the regression equation.

The lipid amount of the EVs is proportional to EV amount, since the lipid amount correlates with the surface area of the EVs and within a known size-based EV population the surface and the EV amount correlates too. The surface area of EVs in a narrow size-range is known or can be calculated. In some embodiments, amount of EVs being in a wider size-range can be quantified based on the size-distribution of the vesicles. The size-distribution may be known or subject to a measurement. Methods for the determination of the EV amount based on the lipid amount are known for the skilled person. The term "determine" may be used interchangeable with the term "calculate".

Lipid components of the biological samples are generally isolated with organic solvents such as methanol, chloroform or methanol-chloroform mixtures. They are usually characterised by chromatographic methods such as thin layer chromatography (TLC), high pressure liquid chromatography (HPLC) and mass spectroscopy (MS), fluorescence labelling methods and colorimetric detections. From chemical point of view, lipids are highly non polar molecules and dissolve mainly in organic solvents. Phospholipids (e.g. phosphatidylcholine, phosphatidylserine), that are the main components of the biological membranes, contain a polar head group making them amphipathic molecules. These amphipathic phospholipids form micelles and stable colloids.

Using the classical lipid characterisation techniques colloidal lipid particles such as liposomes should be avoided as they may causes artefacts and clogging of the equipment. In case of sulfo-phospho-vanillin (SPV) assay based colorimetric detection methods the solvent of the lipids and the standard are organic solvents. The most popular solvent is chloroform while other solvents such as absolute ethanol, chloroform-methanol mixtures, carbon tetrachloride, hexane, DMSO have been applied by different laboratories. Usually different oils e.g.: olive oil, Schizochytrium oil, corn oil, menhaden fish oil and cholesterol or mixture of palmitic and oleic acid (1:1) are used as standard for the reaction. These oils do not form stable colloids unlike phospholipids (e.g. DOPC). Serial dilution of these standards cannot be made in aqueous solutions, application of organic solvents is essential.

Figure 1:
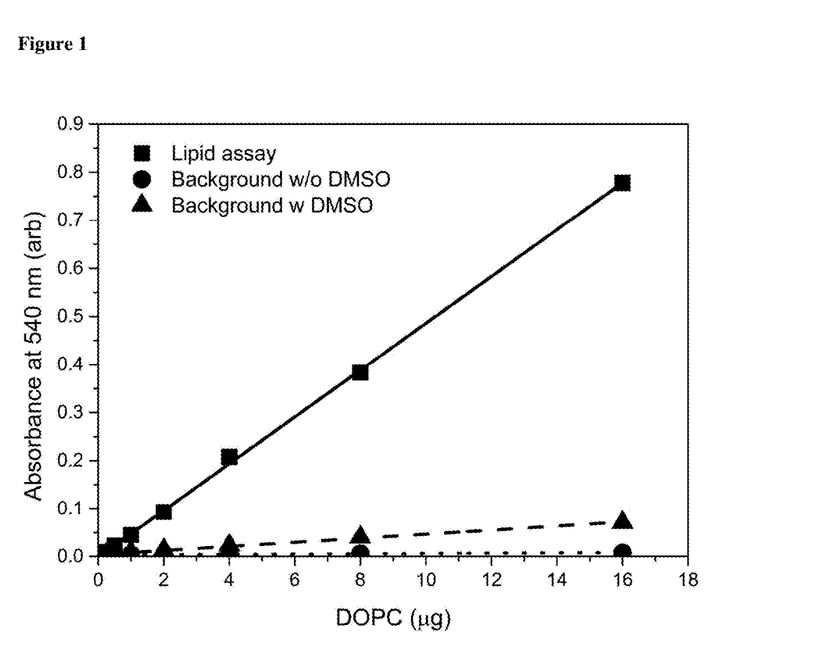
FIG. 1: standard curve after sulfo-phospho-vanillin reaction (SPV reaction, see below); background without DMSO before adding phospho-vanillin reagent and background with DMSO before adding phopho-vanillin reagent. Yellow colour develops when the reaction mixture contains organic solvent (w DMSO–20 μL DMSO+20 μL; 16 μg DOPC in PBS+200 μL 96% sulfuric acid) compared with a sample that does not contain organic solvent (w/o DMSO–40 μL; 16 μg DOPC in PBS+200 μL 96% sulfuric acid) after 20 min incubation at 90° C. (A). Reference concentrations: 0; 0.25; 0.5; 1; 2; 4; 8; 16 μg

Originally the intention was to measure EVs (which by nature behaves as a colloids) with SPV reaction. We have tried to use fish oil and cholesterol dissolved in chloroform as standard, see [10]. Chloroform was added to aqueous EV samples providing the equal handling of the samples. We have observed during these earlier studies that any residual organic solvent caused yellow artificial colours. The intense evaporation of the standard may cause inaccuracy of pipetting and increased concentration over time due to loss of solvent. These effects resulted in reduced sensitivity of the SPV assay and made almost impossible to detect less than 2-5 ug lipids from EV samples. Usually, the overall amount of harvested EVs is 2-5 ug, meaning that at least half of the EV samples had to be used for lipid quantification. Organic solvents also impose health hazards. Importantly, when lipid samples contain organic solvents like chloroform, dimethyl sulfoxide (DMSO) or acetone, a yellowish colour develops. This colour has an influence on the detected absorbance, especially in the lower concentration range. However, even though it shows correlation with the lipid content of the samples, the specificity and sensitivity of this reaction does not enable lipid determination of low lipid concentrations which are characteristic for EV preparations (FIG. 1). This phenomenon is mentioned in the technical notes of a commercial lipid quantification kit that is based on the above mentioned SPV assay. The manufacturer of the kit recommends subtracting this yellowish background colour from the read at 540 nm after SPV reaction (Lipid Quantification Kit, STA-613 Cell Biolabs, Inc.). Thus, the problem is known in the field, but less effective solutions have been provided so far.

The present inventors have, instead of the classically used oil standards, prepared and used a DOPC liposome standard, which allowed using an aqueous environment. In our modified lipid assay we omitted organic solvents from the quantification method, and both our standards and samples are in aqueous phase. Physicochemical properties of these liposomes are very close to those of EVs making the measurements accurate. Application of a suspension containing DOPC liposomes in aqueous solvent as reference, has solved both the problem caused by the yellow artefactual colour and the inaccuracy of pipetting; without organic solvents we do not observe the yellow background colour. Although DOPC was used in our early experiments, it is clear that any phospholipid capable of forming liposomes, can be applied as reference material, for example, sphingomyelin, phosphatidyl serin, phophatidyl ethanonamine.

An optimised phospho-vanillin reagent was also introduced to increase the sensitivity of the lipid assay. The final vanillin concentration was increased 5 times compared to what has been used by Osteikoetxea at al. [10]. The phospho-vanillin reagent remained stable at 4° C. in dark for at least 3 months.

The invention as described above may be applied for quantification of any biological membranes such as plasma membrane, nuclear membrane, ER membrane, intracellular vesicles, mitochondrial membrane, different chloroplast membranes, microsomal membranes, etc. Samples should fulfil the previously mentioned criteria such as they should not contain components reacting with $H_2SO_4$ (sulphuric acid) and should be suspended in aqueous buffer. Residual amount of iodixanol because of its benzyl ring can increase the background of the assay. Methods for providing a preparation containing biological membranes from the sample and are well known for the skilled person. Methods for providing a preparation being in a narrow size are for example those mentioned for the EVs. The further steps of the quantification are the same as described for the EVs, mutatis mutandis.

In order to prove that the method according to the invention is suitable of measuring the lipid content of EV samples, lipid content of 5 mg/mL commercial LDL was measured. LDL is a good and accepted model of EVs with a known approximate lipid content. The protein/lipid (P/L) percentage was found 24.89±1.8% which is in good agreement with the literature data where the P/L percentage was between 23 and 26% [20].

Lipid content of EVs was measured and compared with the new liposome based colorimetric lipid assay and with the previously described ATR-FTIR spectroscopy based method [9]. The detected lipid amounts of mEVs were found equal with the two independent methods while the standard deviation of colorimetric assay was found ten limes lower compared with the ATR-FTIR based method.

By using the aqueous phase DOPC liposome standard instead of lipids dissolved in organic solvents as described previously [10, 15, 16, 18, 19], we have increased the sensitivity of the previous assay [10] by approximately 1 order of magnitude. The increased sensitivity makes possible to measure EVs and other colloidal lipids with LoD ~0.2 ug and LoQ ~0.4 ug. It's sensitivity is now comparable to the one of the frequently used protein assays, the Micro BCA assay. The quantification limit of the method according to the invention, with 20% RSD % is approximately 0.5 μg total lipid with 0.2 μg detection limit (FIG. 5) that makes the assay suitable for routine quantification of EV samples. In our hand, depending on cell and EV type, approximately 2-15% of an EV sample isolated from tissue cultures was sufficient for lipid quantification.

The method according to the invention is not influenced by usual components of EV samples like nucleic acids and proteins (see Table 1).

When isolating EVs with the combined method of gravity driven filtration and differential centrifugation from conditioned medium (even if supplemented with EV depleted serum), certain amount of protein contaminants can be found in the EV-enriched samples (Table 5). The results clearly show that protein measurement of samples give an enormously high value even when isolated from mock (cell free) conditions. Only the method according to the present invention can discriminate between mock and EV containing isolates.

Figure 4:
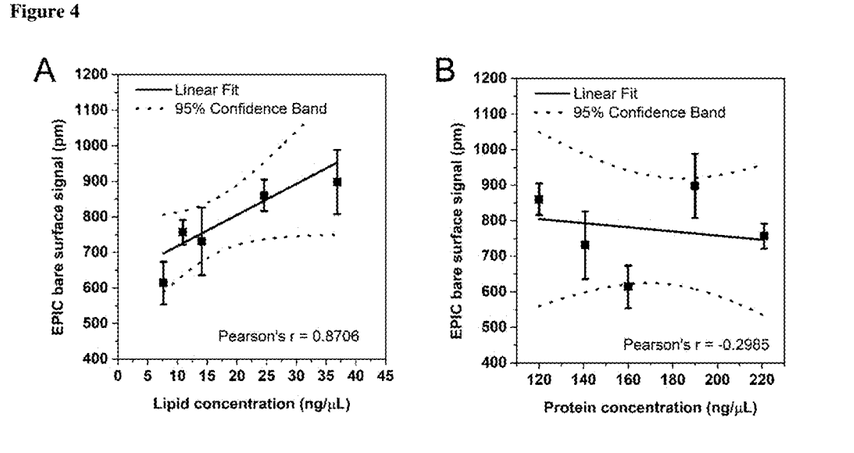
FIG. 4: Correlation between lipid and protein concentration of EVs with the bare surface signal of an EPIC optical biosensor

Results with the EPIC system (see example 11) show that the lipid content of a sample provides a much more reliable standardisation as compared to the standardisation based on total protein concentration of the samples (see FIG. 4). In addition, we compared the DOPC standard of the present invention with a purified lipid standard of a commercial kit. The DOPC and purified lipid standards (in the 0.25-16 μg lipid range) did not differ significantly in the method of the invention. Together with the further tests, this validates the method of the invention.

Our method can be used virtually in any standard laboratories where a fume hood, a thermoblock, and a spectrophotometer are available. The application does not require expensive equipment (unlike IR spectroscopy or MS), therefore it can be an easy, reliable and quick method for quantification of EVs and standardisation of EV experiments.

The following examples are intended solely to illustrate one or more preferred embodiments of the invention and are not to be construed as limiting the scope of the disclosure.

EXAMPLES

Example 1: Cell Lines

AC16 human cardiomyocyte cell line (SCC109) was purchased from Merck and was cultured according to the instructions of the manufacturer. Before EV isolation, AC16 cells were differentiated according to Davidsons work [11]. Cells were cultured in tissue culture flasks coated with 0.02% gelatine (EMD Millipore) and 5 µg/mL fibronectin (Gibco) up to confluency. Once the cells reached confluency, they were cultured for an additional week in DMEM/F12 medium supplemented with 2% horse serum and 1× Insulin-Transferrin-Selenium (all from Gibco). EVs were isolated from serum free conditioned medium.

H9c2 (2-1) BDIX rat heart myoblast cell line was ordered from ECACC through Sigma-Merck. Cells were cultured in DMEM medium (Sigma) supplemented with 10% FBS (Gibco), 1% MEM Non-essential amino acid solution (Sigma), antibiotic-antimycotic solution (Gibco); 2 mM L-Glutamine (EMD Millipore) and 3.51 g/L D-Glucose (Sigma). Before EV isolation, H9c2 cells were differentiated according to Mdnard et al. [12]. Cells were cultured up to confluency, then they were cultured a day in DMEM medium supplemented with 1% FBS (Gibco), and an additional week in DMEM medium supplemented with 1% FBS (Gibco) and 10 nM retinoic acid. EVs were isolated from serum free conditioned medium.

HL1 immortalized mouse cardiomyocyte cell line (SCC065) was ordered from Merck and was cultured according to the instructions of the manufacturer. Once cells reached confluency, they were cultured for an additional day (when spontaneous contractions of the cells were detectable). EVs were isolated from serum free conditioned medium.

THP-1 human leukemic monocyte cell line was ordered from ECACC through Sigma-Merck. Cells were cultured as described previously by Osteikoetxea et al. [13]. The cell line was cultured in RPMI medium containing 10% FBS (Gibco), 2 mM glutamine (EMD Millipore), and 1% antibiotic-antimycotic solution (Gibco). EVs were isolated from serum free conditioned medium.

Example 2: EV Preparation—Isolation from Conditioned Cell Culture Medium

EVs were isolated based on Osteikoetxea et al. [10] with minor changes. Prior to isolation, cells were washed three times with PBS, and EV production was allowed to take place for 24 hours in serum-free medium or in the presence of 12.5% EV-depleted FBS (Gibco). Three different size-based subpopulations were isolated including large (lEV, here referred to as apoptotic bodies), mid-sized (mEV, here referred to as microvesicles) and small (sEV, here referred to as exosomes) EVs by the combination of gravity driven filtration and differential centrifugation. Briefly, cells were removed by centrifugation at 300 g for 10 min at room temperature (RT), and then the supernatant was filtered by gravity through a 5 µm filter (Millipore, Billerica, MA) and submitted to a 2,000 g centrifugation for 30 min at 4° C. to pellet lEVs (Avanti J-XP26 centrifuge, JA 25.15 rotor, Beckman Coulter Inc.). The supernatant was next filtered by gravity through a 0.8 µm filter (Millipore), and centrifuged at 12,500 g for 40 min at 4° C. to pellet mEVs (Avanti J-XP26 centrifuge, JA 25.15 rotor, Beckman Coulter Inc.). Finally the supernatant was filtered by gravity through a 0.22 µm filter (Millipore) and ultracentrifuged in an Optima MAX-XP bench top ultracentrifuge with MLA-55 rotor (Beckman Coulter Inc.) at 100,000 g for 70 min at 4° C. to pellet sEVs. Each EV pellet was re-suspended once in phosphate-buffer-saline (PBS), and re-centrifuged under the same conditions as used originally for pelleting.

Example 3: Preparation of the Lipid Standard—Stock Suspension

As a lipid standard, 1,2-Dioleoyl-sn-glycero-3-phosphocholine (DOPC) liposomes were used in 1 mg/mL concentration. DOPC was purchased form Sigma-Aldrich in lyophilised form. 1 mg DOPC was dissolved in 1 mL chloroform (Reanal) in a 2 ml volume test tube. Chloroform was evaporated at 60° C. in a thermoblock (Labnet) under a fume hood. Next, PBS was added to the dried DOPC cake, and the tube was vortexed intensively for 2 min at maximum speed (Fisherbrand). The resulting crude liposome suspension was then sonicated with 35 kHz (Emmi 20, EMAG) at 45° C. for 10 min followed by an additional 2 min intensive vortexing. The obtained liposome standard was stable at 4° C. for at least 3 months, however, immediately before use, intensive vortexing of the standard was essential.

Example 4: Preparation of Phospho-Vanillin Reagent

An optimised phospho-vanillin reagent was introduced to increase the sensitivity of the lipid assay. 50 mg vanillin (Sigma) was dissolved in 50 mL of 17% phosphoric acid (Sigma). Thus, the final vanillin concentration was increased 5 times compared to what has been used by Osteikoetxea at al. [10].

The phospho-vanillin reagent was stable at 4° C. in dark for at least 3 months.

Example 5: Calibration and Linear Regression

Figure 3:
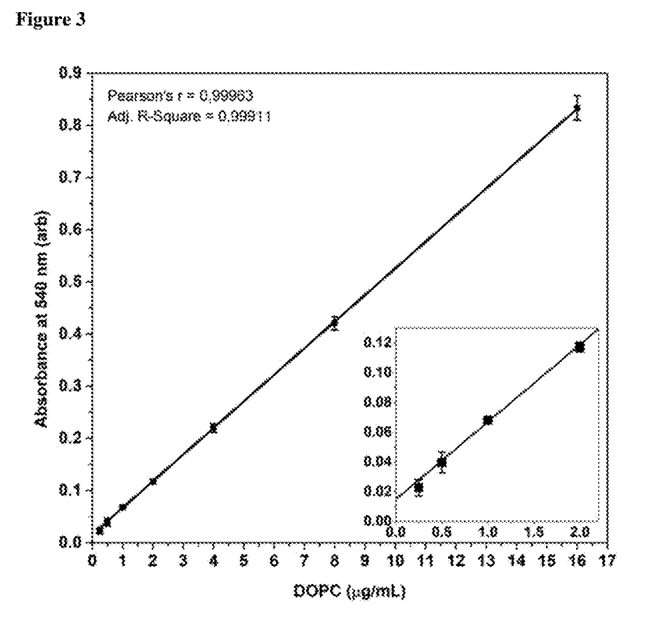
FIG. 3: Standard curve of the improved lipid assay

We set the standard curve from 0.25-16 µg DOPC in 40 µL (6.25-400 ng/mL; n=3) using the new liposome standard and the method of the invention with the increased vanillin concentration. As shown in FIG. 3, the correlation (Pearson's r value) between the absorbance at 540 nm and the lipid concentration is close to 1, therefore, the modified assay is suitable for detection of lipids and liposomes in aqueous phase.

Example 6: Determination of Lipid Content of an EV Preparation

Two hundred µL of 96% sulfuric acid (Molar Chemicals) was added either to 40 µl of reference suspension or to 40 µl EV preparation suspended in PBS or deionised water or NaCl HEPES buffer in 1.5 mL test tubes (Safe-Lock tubes, 1.5 mL, 0030 120-086, Eppendorf AG, Germany).

After a brief vortexing, the open test tubes were incubated at 90° C. (AccuBlock digital dry batch, Labnet) in a fume hood for 20 min. Tubes were cooled down to RT by placing for at least 5 min at 4° C., and 120 µL of phospho-vanillin reagent was added to each tube and was vortexed. Next, 2801 of each sample was transferred to a 96 well plate (Thermo) and colour reaction was allowed to develop for 1 h at 37° C. Absorbance at 540 nm was determined with a plate reader (Multiskan MS, Labsystems).

Example 7: Sample Consumption

One of the next key question was if the modified lipid assay was suitable of measuring the lipid content of EV preparations. As Table1 shows, 15% of the EV preparations were enough to give readily detectable lipid results with the method of the invention. EVs were isolated from the conditioned media of two T175 confluent tissue culture flasks (24 h serum free) of AC16 and HL1 cells. Volume of the conditioned medium was 24 mL (2 times 12 mL). 30 µL of EV preparation was obtained in every size fraction. 16% of EVs (5 µL out of 30 µL) was used for lipid measurements.

TABLE 1

| Cell type | EV type | Approx. EV size | Total lipid content of EVs |
|---|---|---|---|
| AC16 | Big size EVs | 800-1500 nm | 37.84 µg |
| AC16 | Medium size EVs | 200-800 nm | 21.60 µg |
| AC16 | Small size EVs | <200 nm | 9.74 µg |
| HL1 | Big size EVs | 800-1500 nm | 36.34 µg |
| HL1 | Medium size EVs | 200-800 nm | 57.29 µg |
| HL1 | Small size EVs | <200 nm | 16.63 µg |

Example 8: Indirect Determination of EVs Lipid Concentration Using ATR-FTIR Spectroscopy IR spectra were recorded by the means of a Varian 2000 FTIR spectrometer (Varian Inc., US) equipped with an MCT (Mercury-Cadmium-Telluride) detector and a single reflection diamond ATR accessory (Specac Ltd, UK). 3 µL of samples was placed on the top of the diamond ATR crystal and dry film spectra were collected (64 scans, 2 cm$^{-1}$ spectral resolution) after solvent evaporation. At least 3 parallel measurements were done. A spectroscopic protein-to-lipid ratio ($P/L_{spectr}$) was determined using the protocol described in [9]. Briefly, after PBS background spectral subtraction, the relative amount of protein is estimated by the integrated intensity of protein Amide I band (around 1650 cm$^{-1}$) while the lipid content is approximated by the integrated area of C—H stretching bands from the 3020-2800 cm$^{-1}$ wavenumber region. Conversion of the spectroscopic protein-to-lipid ratio ($P/L_{spectr}$) to nominal protein-to-lipid ratio ($P/L_{nom}$) requires an adequate calibration curve. For this purpose BSA-Brain Total Lipid Extract mixtures prepared in PBS buffer with varying protein-to-lipid ratios (from 0.2 to 4 mg/mg) was used.

Example 9: Determination of Protein Content of EVs Using BCA

Protein concentration of EVs were determined with Micro BCA Protein Assay kit (Thermo) according to the instruction of the manufacturer. Briefly, EVs were diluted 5 to 10 times and were lysed with 0.5% Triton X-100 (Sigma) and 0.05% SDS (Sigma). Colour was developed for 1 h at 60° C. and absorbance at 562 nm was measured (NanoDrop NP-1000 ThermoFisher)

Example 10: Comparison of the Method of the Invention and ATR-FTIR Method

The method was validated with the help of mEVs (100-800 nm diameter) obtained from serum free conditioned media of differentiated cells of H9c2 and AC16 cell lines. Lipid content of mEV was measured (according to example 6) and compared with the ATR-FTIR spectroscopy based method (example 8). Total lipid as presented in Table 2 was calculated from spectroscopic and nominal P/L ratio with the help of the protein concentration determined by Micro BCA test (example 9). Result of the new lipid assay and ATR-FTIR have been summarised in Table 3. The detected lipid amounts of mEVs were found equal with the two independent methods while the standard deviation of colorimetric assay was found ten times lower compared with the ATR-FTIR based method.

TABLE 2

| | $P/L_{spectr}$ | $P/L_{nom}$ | Protein conc ng/ml | Calculated lipid conc ng/ml |
|---|---|---|---|---|
| AC16 mEV | 0.3587 ± 0.0716 | 0.8178 ± 0.2524 | 86.6 | 113.9 ± 39.47 |
| H9c2 mEV | 0.3516 ± 0.1068 | 0.7928 ± 0.3761 | 101.7 | 144.5 ± 68.57 |

TABLE 3

| Sample | Protein concentration (ng/µL) | Lipid concentration - measured according to the method of the invention (ng/µL) | Lipid concentration - calculated based on the IR method (ng/µL) |
|---|---|---|---|
| mEV H9c2 | 101.7 ± 2.9 | 114.5 ± 3.1 | 144.5 ± 68.6 |
| mEV AC16 | 86.6 ± 2.58 | 105.1 ± 1.5 | 113.9 ± 39.4 |

Example 11: Determination of EV-Related Surface Adhesion Signal

EV related surface adhesion signal of THP-1 cell-derived small EVs was determined as previously described by Németh et al. [17]. For the measurements, an EPIC Bench-Top system (Corning Inc.) was used with Corning EPIC 384 Well Cell Assay Microplates. Changes in the refractive index caused by adhesion of EVs onto the surface were recorded. Bare surface signal correlated with the quantity of EVs.

In this test, the correlation between the amount of EVs and either the protein or the lipid concentration was studied. Small sized EVs were isolated from serum-free conditioned medium of THP-1 cells. The bare surface EPIC signal was compared with the protein concentration (measured with Micro BCA method) and the lipid concentration (measured with method according to the invention). FIG. 4A shows the correlation between the lipid concentration and the EPIC bare surface signal. B shows the same between protein concentration and the EPIC bare surface signal. It is clear that the bare surface signal of EPIC has a good correlation with the lipid concentration of the samples while it does not correlate with the protein concentration.

Example 12: Determination of Size Distribution and Concentration of EVs

Size-distribution and concentration of H9c2-derived mEVs were determined by tuneable resistive pulse sensing analysis using a qNano instrument (IZON Science) as described previously [17]. Two-fold dilution of the sample (derived from 24 mL cell supernatant) was prepared in 0.2 µm filtered PBS and was measured by qNano. At least 700 particles were counted using 10 mbar pressure and NP400 nanopore membranes. Calibration was performed using known concentration of beads CPC400G (mean diameter: 340 nm) from IZON diluted 1:1,000 in 0.2 µm filtered PBS. Results were evaluated using IZON Control Suite 3.2 software.

Figure 2:
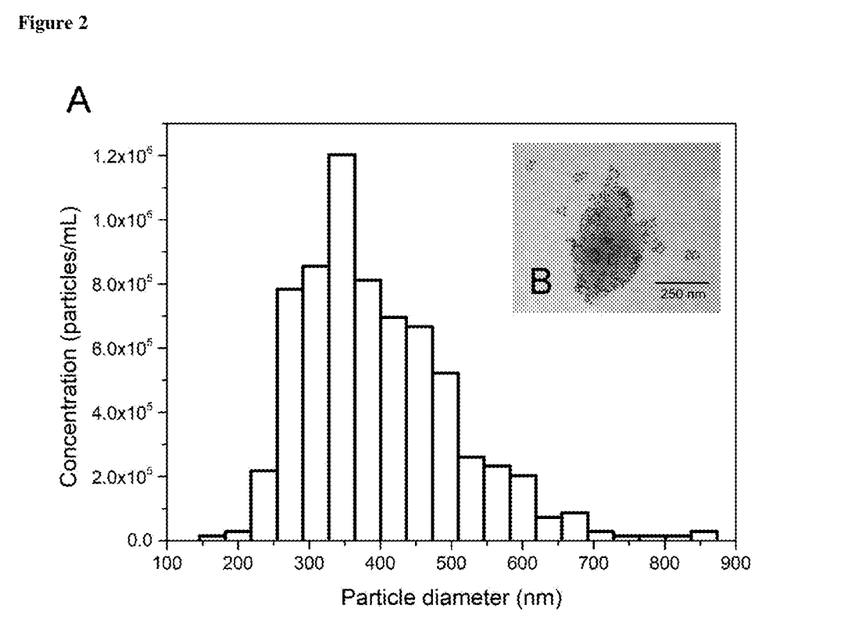
FIG. 2: Particle size and concentration of midsized, CD63 positive EVs isolated from the conditioned medium of H9c2 differentiated cardiomyoblasts

Particle size and concentration of the CD63 positive EV particles (H9c2 cell line) were determined by qNano (FIG. 2). A: the figure shows particle size and concentration obtained by qNano of an EV sample isolated from the conditioned medium of H9c2 cells containing midsized particles. B: electron micrograph of the midsized H9c2 EVs. CD63 protein on the electron micrograph has been immunologically labelled by 10 nm gold particles (see example 13).

Total membrane surface/mL was calculated from the diameter of the particles and their concentration. Lipid content of the samples was determined by the optimised lipid assay. We have found that the EV sample contained $2.66 \times 10^{-5}$ g lipid/m$^2$ based on the lipid amount obtained by the method of the invention while $3.59 \times 10^{-3}$ g lipid/m$^2$ is expected if all the particles detected by qNano had been EVs and we had not been calculated by the protein content of the EV membranes [21].

Example 13: Detection of CD63 Positive H9c2 mEVs by Transmission Electron Microscopy For transmission electron microscopy, 2 µL of sample resuspended in 0.22 µm filtered PBS was placed onto the surface of 300 mesh formvar-coated Ni grids, and was incubated for 10 min at RT. Then the residual solution was removed, and samples were fixed (10 min at RT) by 0.22 µm filtered 4% paraformaldehyde in PBS, and washed 3 times for 5 min, at RT with PBS. For blocking, 1 hr incubation with 5% BSA (Sigma) in 0.22 µm filtered PBS was used. Primary antibody, polyclonal rabbit anti-CD63 IgG (H-193, sc-15363, Santa Cruz Biotechnology) was applied overnight at 4° C. in 1:50 dilution in 0.22 µm filtered 5% BSA in PBS. After washes (3 times 5 min with 0.22 µm filtered 5% BSA), a secondary antibody, polyclonal goat anti-rabbit IgG 10 nm gold pre-adsorbed, was used for 3 h at RT. Samples were than washed 3 times for 5 min with 0.22 µm filtered 5% BSA, 3 times for 5 min with 0.22 µm filtered PBS and 3 times for 5 min with purified water. Finally, permanent fixation by 2% glutaraldehyde was applied for 10 min at RT followed by 3 times 5 min washes with purified water. For background contrasting, 2% phosphotungstic acid was used (10 min RT) followed by 3 times 1 min washes. Samples were examined by JEOL 1011 transmission electron microscope (Japan).

Example 14: Robustness

To address the question of interference with the optimised assay by potential components of EV preparations, we added increasing concentrations of proteins and nucleic acids (DNA) to 2.5 µg DOPC liposomes, and assessed the 540 nm absorbance values. Bovine serum albumin (BSA) was used as a test protein and genomic DNA extracted from *Saccharomyces cerevisiae* cells was us as test nucleic acids. As summarised in Table 4, neither protein nor DNA concentration of the sample affected the lipid detection by the optimised assay.

TABLE 4

| Protein concentration | Absorbance (arb) | | Replicates | Student t-test | One-way ANOVA |
|---|---|---|---|---|---|
| (µg) | average | SD | n | p= | |
| 0.0 | 0.1839 | 0.0213 | 6 | | |
| 0.63 | 0.1830 | 0.0076 | 3 | 0.9463 | |
| 1.25 | 0.1830 | 0.0176 | 3 | 0.9512 | $F(0.2894) < F_{crit}$ |
| 2.50 | 0.1953 | 0.0068 | 3 | 0.4076 | (2.6143) |
| 5.00 | 0.1917 | 0.0184 | 3 | 0.6642 | |
| 10.00 | 0.1867 | 0.0101 | 3 | 0.8414 | Protein (BSA) |
| 20.00 | 0.1933 | 0.0105 | 3 | 0.5020 | concentration |
| 40.00 | 0.1842 | 0.0262 | 3 | 0.9891 | significantly do not change the mean absorbance at 540 nm |

| DNA concentration | Absorbance (arb) | | Replicates | Student t-test | One-way ANOVA |
|---|---|---|---|---|---|
| (ng) | average | SD | n | p= | |
| 0.0 | 0.1355 | 0.0178 | 6 | | |
| 15.6 | 0.1270 | 0.0066 | 3 | 0.4629 | |
| 31.3 | 0.1273 | 0.0176 | 3 | 0.5366 | $F(0.3354) < F_{crit}$ |
| 62.5 | 0.1323 | 0.0074 | 3 | 0.7822 | (2.5435) |
| 125.0 | 0.1410 | 0.0174 | 3 | 0.6740 | |
| 250.0 | 0.1310 | 0.0017 | 3 | 0.6862 | DNA concentration |
| 500.0 | 0.1313 | 0.0157 | 3 | 0.7428 | significantly do not |
| 1000.0 | 0.1300 | 0.0121 | 3 | 0.6500 | change the mean absorbance at 540 nm |

In addition, here we show an example in which EVs were isolated from the conditioned medium samples supplemented with 12.5% EV-depleted serum (Gibco). Protein concentration of midsized (mEV) and small sized (sEV) vesicles were determined by Micro BCA kit (Thermo). The lipid concentration was assessed by the method of the invention. EVs (mEVs AC16 and sEVs AC16) were isolated form 24 mL conditioned medium (24 h) of two confluent T175 flasks of AC16 cell culture. The tissue culture medium contained 12.5% EV-depleted serum (Gibco). mEV medium and sEV medium are technical controls of 24 mL non-conditioned medium, containing 12.5% EV depleted serum (Gibco). The protein and lipid content of the EV preparations were compared to values obtained from identically treated, non-conditioned medium samples containing 12.5% EV-depleted serum (Table 5).

As shown in the table, all samples contained significant and relatively similar amounts of protein. However, lipid content was measurable only from the conditioned media.

TABLE 5

| | Protein concentration ng/ml | Lipid concentration ng/mL | Protein/lipid ratio (medium background subtracted) |
|---|---|---|---|
| mEV AC16 | 205.00 | 21.83 | 2.52 |
| sEV AC16 | 206.67 | 17.16 | 2.04 |
| mEV Medium | 150.00 | ND | N/A |
| sEV Medium | 171.67 | ND | N/A |

Figure 5:
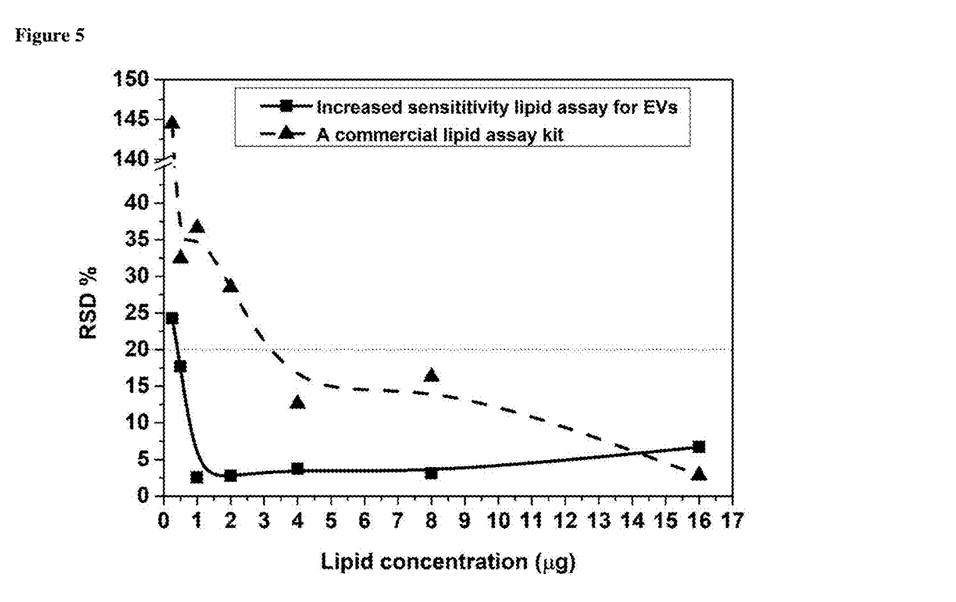
FIG. 5: RSD % of the optimised lipid assay and of a commercial assay

Example 15: Comparison of the Optimised Lipid Assay with the Commercial Lipid Kit First, we have compared the standard curves of the commercial kit (following the instructions of the manufacturer) and our optimised lipid assay. We determined the relative standard deviation (RSD) % values (FIG. 5). As shown in the figure, the widely accepted 20% RSD value [22] (indicated by dot lines) was reached at approximately 0.4 µg total lipid in 40 µL (10 ng/µL) with the optimised lipid assay as compared to 1.6 µg in 20 µL (80 ng/µL) total lipid in the case of the commercial lipid kit. This means that the sensitivity of the optimised lipid assay is approximately one order of magnitude higher than that of the commercial assay.

Figure 6:
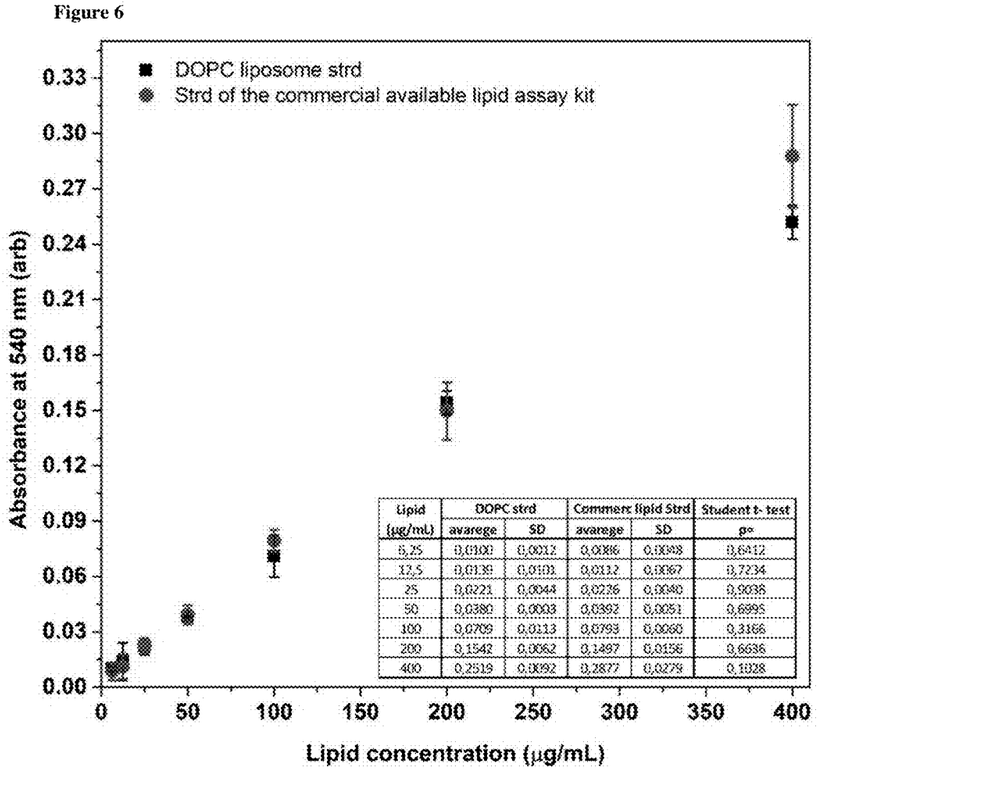
FIG. 6: Comparison between the DOPC standard and the standard of the commercial lipid kit

In addition, we validated the newly introduced DOPC liposome standard. To this end, we measured the purified lipid standard of the commercial kit along with our DOPC standard by our novel, optimised assay. Since the commercial standard is dissolved in DMSO in the kit, we ensured that the 40 µL sample volume contained 10 µL DMSO and 30 µL PBS in case of both lipid standards. The presence of DMSO explains the lower sensitivity of the assay in this case (FIG. 6). The DOPC and purified lipid standards (in the 0.25-16 µg lipid range) did not differ significantly in our assay.

REFERENCES

1. Consortium E-T, Van Deun J, Mestdagh P, et al. EV-TRACK: transparent reporting and centralizing knowledge in extracellular vesicle research. Nature Methods. 2017 02/28/online; 14:228. doi: 10.1038/nmeth.4185
2. Pocsfalvi G, Stanly C, Vilasi A, et al. Mass spectrometry of extracellular vesicles. Mass Spectrometry Reviews. 2016; 35(1):3-21. doi: 10.1002/mas.21457.
3. Yáñez-Mó M, Siljander P R M, Andreu Z, et al. Biological properties of extracellular vesicles and their physiological functions. Journal of Extracellular Vesicles. 2015 05/14 12/22/received 02/24/revised 03/10/accepted; 4:10.3402/jev.v4.27066. doi: 10.3402/jev.v4.27066. PubMed PMID: PMC4433489.
4. Maas S L N, de Vrij J, van der Vlist E J, et al. Possibilities and limitations of current technologies for quantification of biological extracellular vesicles and synthetic mimics. Journal of Controlled Release. 2015 2015/02/28/; 200:87-96.
5. Lötvall J, Hill A F, Hochberg F, et al. Minimal experimental requirements for definition of extracellular vesicles and their functions: a position statement from the International Society for Extracellular Vesicles. Journal of Extracellular Vesicles. 2014 12/22; 3:10.3402/jev.v3.26913. doi: 10.3402/jev.v3.26913. PubMed PMID: PMC4275645.
6. Tkach M, Kowal J, Théry C. Why the need and how to approach the functional diversity of extracellular vesicles. Philosophical Transactions of the Royal Society B: Biological Sciences. 2018 2018-01-05 00:00:00; 373.
7. György B, Módos K, Pállinger É, et al. Detection and isolation of cell-derived microparticles are compromised by protein complexes resulting from shared biophysical parameters [10.1182/blood-2010-09-307595]. Blood. 2011; 117(4):e39.
8. Melo S A, Luecke L B, Kahlert C, et al. Glypican-1 identifies cancer exosomes and detects early pancreatic cancer [Article]. Nature. 2015 06/24/online; 523:177. doi: 10.1038/nature14581
9. Mihály J, Deák R, Szigyártó I C, et al. Characterization of extracellular vesicles by IR spectroscopy: Fast and simple classification based on amide and CH stretching vibrations. Biochimica et Biophysica Acta (BBA)—Biomembranes. 2017 2017/03/01/; 1859(3):459-466.
10. Osteikoetxea X, Balogh A, Szabó-Taylor K, et al. Improved Characterization of EV Preparations Based on Protein to Lipid Ratio and Lipid Properties. PLOS ONE. 2015; 10(3):e0121184. doi: 10.1371/journal.pone.0121184.
11. Davidson M M, Nesti C, Palenzuela L, et al. Novel cell lines derived from adult human ventricular cardiomyocytes. Journal of Molecular and Cellular Cardiology. 2005 2005/07/01/; 39(1):133-147.
12. Mdnard C, Pupier S, Mornet D, et al. Modulation of L-type Calcium Channel Expression during Retinoic Acid-induced Differentiation of H9C2 Cardiac Cells. Journal of Biological Chemistry. 1999 Oct. 8, 1999; 274(41):29063-29070. doi: 10.1074/jbc.274.41.29063.
13. Osteikoetxea X, Sodar B, Nemeth A, et al. Differential detergent sensitivity of extracellular vesicle subpopulations. Org Biomol Chem. 2015 Oct. 14; 13(38):9775-82. doi: 10.1039/c5ob01451d. PubMed PMID: 26264754; eng.
14. Akbarzadeh A, Rezaei-Sadabady R, Davaran S, et al. Liposome: classification, preparation, and applications. Nanoscale Research Letters. 2013 02/22 01/05/received 01/22/accepted; 8(1):102-102. doi: 10.1186/1556-276X-8-102. PubMed PMID: PMC3599573.
15. Frings C S, Fendley T W, Dunn R T, et al. Improved Determination of Total Serum Lipids by the Sulfo-Phospho-Vanillin Reaction. Clinical Chemistry. 1972; 18(7): 673.
16. Frings C S, Dunn R T. A Colorimetric Method for Determination of Total Serum Lipids Based on the Sulfo-phospho-vanillin Reaction. American Journal of Clinical Pathology. 1970; 53(1):89-91. doi: 10.1093/ajcp/53.1.89.
17. Németh A, Orgovan N, Sódar B W, et al. Antibiotic-induced release of small extracellular vesicles (exosomes) with surface-associated DNA. Scientific Reports. 2017 2017/08/15; 7(1):8202. doi: 10.1038/s41598-017-08392-1.
18. Cheng Y-S, Zheng Y, VanderGheynst J S. Rapid Quantitative Analysis of Lipids Using a Colorimetric Method in a Microplate Format. Lipids. 2011 2011/01/01; 46(1): 95-103. doi: 10.1007/s11745-010-3494-0.
19. Johnson K R, Ellis G, Toothill C. The sulfophosphovanillin reaction for serum lipids: a reappraisal. Clinical Chemistry. 1977; 23(9):1669.
20. Kuchinskiene Z, Carlson L A. Composition, concentration, and size of low density lipoproteins and of subfractions of very low density lipoproteins from serum of normal men and women. Journal of Lipid Research. 1982 Jul. 1, 1982; 23(5):762-9.
21. Reddy A S, Warshaviak D T, Chachisvilis M. Effect of membrane tension on the physical properties of DOPC lipid bilayer membrane. Biochimica et Biophysica Acta (BBA)—Biomembranes. 2012 2012/09/01/; 1818(9): 2271-2281.
22. ICH Quality Guidelines: An Implementation Guide. Teasdale A, Elder D, Nims R W, editors.: Wiley; 2017.
23. Sódar B W, Kittel Á, Pálóczi K, et al. Low-density lipoprotein mimics blood plasma-derived exosomes and microvesicles during isolation and detection. Scientific Reports. 2016 04/18 01/14/received 03/21/accepted; 6:24316. doi: 10.1038/srep24316. PubMed PMID: PMC4834552.

The invention claimed is:
1. Method for quantification of extracellular vesicles (EVs) in a sample comprising
   a) providing an EV preparation from the sample, the EV preparation being an aqueous suspension comprising EVs;

b) contacting the EV preparation of step a) with sulphuric acid and subsequently with phospho-vanillin reagent and then allowing a colour reaction to develop, to obtain a coloured solution;
c) measuring the absorbance of the coloured solution of step b);
d) comparing the absorbance measured in step c) to the absorbance of one or more reference suspension and calculating the amount of lipids in the EV preparation from the result of said comparison;
e) calculating the amount of EVs in the EV preparation of step a) from the amount of lipids calculated in step d);
characterized in that
the EV sample preparation in step a) is substantially free of organic solvents;
the reference suspension in step d) comprises liposomes suspended in aqueous solvent, wherein the liposomes are formed from 1,2-dioleoyl-sn-glycero-3-phosphocholine (DOPC), and wherein the aqueous solvent is an aqueous buffer selected from PBS, NaCl-HEPES, MES, TRIS, physiological NaCl solution or DPBS; and
the reference suspension is substantially free of organic solvents.

2. Method according to claim 1 wherein the reference suspension in step d) is a diluted stock suspension comprising the liposomes suspended in aqueous solvent, and the stock suspension is substantially free of organic solvents.

3. Method according to claim 1, characterized in that the EV preparation of step a) contains EVs having a size range wherein the difference between the lower limit and the upper limit of the range is lower than 600 nm.

4. Method according to claim 1, characterized in that the EV preparation of step a) contains EVs in a size range of less than 200 nm or from 200 nm to about 800 nm or from 800 nm to about 5000 nm.

5. Method according to claim 1, wherein step b) comprises
b1) contacting the solution of step a) with sulphuric acid and mixing with vortex
b2) incubating the mixture of b1) at 90° C. for 20 min, then cooling to room temperature
b3) adding phospho-vanillin reagent and mixing with vortex
b4) incubating the mixture of b3) for 1 h at 37° C. to enable the colour reaction to develop.

6. Method according to claim 1 having a quantification limit, with 20% relative standard deviation (RSD) value, of approximately 0.5 µg total lipid.

7. Method according to claim 6 with a 0.2 µg total lipid detection limit.

8. Method according to claim 1 wherein the preparation contains less than 5 µg total lipid.

9. Method for quantification of lipids in a sample comprising extracellular vesicles (EVs), the method comprising the step of
a) providing an EV preparation from the sample, the EV preparation being an aqueous suspension comprising EVs;
b) contacting the EV preparation of step a) with sulphuric acid and subsequently with phospho-vanillin reagent and then allowing a colour reaction to develop, to obtain a coloured solution;
c) measuring the absorbance of the coloured solution of step b);
d) comparing the absorbance measured in step c) to the absorbance of one or more reference suspension and calculating the amount of lipids in the EV preparation from the result of said comparison;
characterized in that
the EV sample preparation in step a) is substantially free of organic solvents;
the reference suspension in step d) comprises liposomes suspended in aqueous solvent, wherein the liposomes are formed from 1,2-dioleoyl-sn-glycero-3-phosphocholine (DOPC), and wherein the aqueous solvent is an aqueous buffer selected from PBS, NaCl-HEPES, MES, TRIS, physiological NaCl solution or DPBS; and
the reference suspension is substantially free of organic solvents.

10. Method for quantification of biological membranes in a sample comprising
a) providing a preparation from the sample, the preparation comprising biological membranes in an aqueous suspension;
b) contacting the preparation of step a) with sulphuric acid and subsequently with phospho-vanillin reagent and then allowing a colour reaction to develop, to obtain a coloured solution;
c) measuring the absorbance of the coloured solution of step b) to obtain a preparation absorbance value, and measuring the absorbance of one or more reference solution prepared from a reference suspension to obtain a reference absorbance value;
d) comparing the preparation absorbance value and the one or more reference absorbance value measured in step c) to the absorbance of one or more reference suspension and calculating the amount of lipids in the preparation from the result of said comparison;
e) calculating the amount of membranes in the preparation of step a) from the amount of lipids calculated in step d);
characterized in that
the EV sample preparation in step a) is substantially free of organic solvents;
the reference suspension in step d) comprises liposomes suspended in aqueous solvent, wherein the liposomes are formed from 1,2-dioleoyl-sn-glycero-3-phosphocholine (DOPC), and wherein the aqueous solvent is an aqueous buffer selected from PBS, NaCl-HEPES, MES, TRIS, physiological NaCl solution or DPBS; and
the reference suspension is substantially free of organic solvents.

* * * * *